United States Patent
Takahashi et al.

(10) Patent No.: US 10,588,875 B2
(45) Date of Patent: Mar. 17, 2020

(54) ORAL COMPOSITION

(71) Applicant: KAO CORPORATION, Tokyo (JP)

(72) Inventors: Noritaka Takahashi, Taito-ku (JP); Ikuhisa Ichimura, Chiba (JP); Takuya Asada, Yoshikawa (JP); Susumu Nakatsu, Ichikawa (JP)

(73) Assignee: KAO CORPORATION, Tokyo (JP)

( * ) Notice: Subject to any disclaimer, the term of this patent is extended or adjusted under 35 U.S.C. 154(b) by 34 days.

(21) Appl. No.: 15/774,103

(22) PCT Filed: May 31, 2016

(86) PCT No.: PCT/JP2016/066016
§ 371 (c)(1),
(2) Date: May 7, 2018

(87) PCT Pub. No.: WO2017/081877
PCT Pub. Date: May 18, 2017

(65) Prior Publication Data
US 2018/0325848 A1 Nov. 15, 2018

(30) Foreign Application Priority Data
Nov. 9, 2015 (WO) ................. PCT/JP2015/081477

(51) Int. Cl.
| | | |
|---|---|---|
| *A61K 31/19* | (2006.01) | |
| *A61K 31/355* | (2006.01) | |
| *A61K 8/60* | (2006.01) | |
| *A61K 47/26* | (2006.01) | |
| *A61K 47/22* | (2006.01) | |
| *A61K 47/12* | (2006.01) | |
| *A61K 9/06* | (2006.01) | |
| *A61K 9/00* | (2006.01) | |
| *A61P 1/02* | (2006.01) | |
| *A61K 47/02* | (2006.01) | |
| *A61K 47/10* | (2017.01) | |
| *A61K 47/14* | (2017.01) | |

(52) U.S. Cl.
CPC ............... *A61K 31/19* (2013.01); *A61K 8/60* (2013.01); *A61K 9/006* (2013.01); *A61K 9/0063* (2013.01); *A61K 9/06* (2013.01); *A61K 31/355* (2013.01); *A61K 47/02* (2013.01); *A61K 47/10* (2013.01); *A61K 47/12* (2013.01); *A61K 47/14* (2013.01); *A61K 47/22* (2013.01); *A61K 47/26* (2013.01); *A61P 1/02* (2018.01)

(58) Field of Classification Search
CPC .............................. A61K 31/19; A61K 31/355
See application file for complete search history.

(56) References Cited

U.S. PATENT DOCUMENTS

| 5,348,733 A | 9/1994 | Morishima et al. |
| 7,569,274 B2 * | 8/2009 | Besse ..................... A61K 9/143 |
| | | 427/212 |

FOREIGN PATENT DOCUMENTS

| JP | 2004-250381 A | 9/2004 |
| JP | 2005-289917 A | 10/2005 |
| JP | 2007-45786 A | 2/2007 |
| JP | 2011-144160 A | 7/2011 |
| JP | 2011-168557 A | 9/2011 |
| JP | 2017-214307 A | 12/2017 |
| JP | 2017-214319 A | 12/2017 |
| JP | 2017-214347 A | 12/2017 |
| JP | 2017-214371 A | 12/2017 |
| JP | 2018-20979 A | 2/2018 |
| WO | WO 2014/087955 A1 | 6/2014 |

OTHER PUBLICATIONS

International Search Report dated Aug. 23, 2016 in PCT/JP2016/066016 filed May 31, 2016.
Extended European Search Report dated Jun. 14, 2019 in European Patent Application No. 16863841.9, 9 pages.

* cited by examiner

*Primary Examiner* — Jennifer M Kim
(74) *Attorney, Agent, or Firm* — Oblon, McClelland, Maier & Neustadt, L.L.P.

(57) ABSTRACT

The present invention relates to an oral composition showing increased adsorption performance of an oil-soluble medicinal ingredient such as glycyrrhetinic acid and tocopherol to the gums and oral mucosa. The invention relates to an oral composition comprising the following ingredients (A), (B), (C), and (D): (A) 0.01 mass % or more and 2.5 mass % or less of one or more oil-soluble medicinal ingredients selected from the group consisting of glycyrrhetinic acid, tocopherol, and a tocopherol derivative; (B) 4 mass % or more and 30 mass % or less of a higher alcohol having 12 or more and 22 or less carbon atoms comprising (b1) cetanol and (b2) stearyl alcohol; (C) 0.1 mass % or more and 10 mass % or less of a surfactant including one or more selected from the group comprising of (c1) a nonionic surfactant selected from the group consisting of sorbitan fatty acid ester and polyoxyethylene sorbitan fatty acid ester, and (c2) an anionic surfactant being a fatty acid having 12 or more and 22 or less carbon atoms or a salt thereof; and (D) water, wherein a mass ratio of the content of (E) an oil agent other than ingredients (A), (B), and (C) and a flavoring agent to the content of ingredient (B), ((E)/(B)), is less than 1; and the content of (F) an abrasive powder comprising a polyvalent metal is 5 mass % or less.

18 Claims, 1 Drawing Sheet

ORAL COMPOSITION

FIELD OF THE INVENTION

The present invention relates to an oral composition.

BACKGROUND OF THE INVENTION

For example, glycyrrhetinic acid and tocopherol capable of providing a variety of pharmacological effects to oral compositions have been conventionally widely used as medicinal ingredients. However, these ingredients have low solubility in water and therefore need some measures to ensure good storage stability. For example, the liquid oral composition described in Patent Literature 1 contains a specific amount of, for example, allantoin to enhance the dispersibility and long-term storage stability of β-glycyrrhetinic acid. In Patent Literature 2, a dentifrice composition contains a specific polyoxyethylene hydrogenated castor oil and an anionic surfactant and is filled in a specific container to maintain stable blending of, for example, a glycyrrhetinic acid after long-term storage.

Patent Literature 3 discloses a dentifrice composition exhibiting excellent medicinal effects and having enhanced persistence by containing an active ingredient such as tocopherols and an oily ingredient, as well as a sucrose fatty acid ester and an anionic surfactant, each at specific mass ratios. The dentifrice composition described in Patent Literature 4 contains a specific amount of a specific peppermint oil together with the above-mentioned active ingredient and a surfactant to express good flavor, in addition to the excellent medicinal effects.
(Patent Literature 1) JP-A-2011-168557
(Patent Literature 2) JP-A-2004-250381
(Patent Literature 3) JP-A-2005-289917
(Patent Literature 4) JP-A-2007-45786

SUMMARY OF THE INVENTION

The present invention relates to an oral composition comprising the following ingredients (A), (B), (C), and (D):

(A) 0.01 mass % or more and 2.5 mass % or less of one or more oil-soluble medicinal ingredients selected from the group consisting of glycyrrhetinic acid, tocopherol, and a tocopherol derivative;

(B) 4 mass % or more and 30 mass % or less of a higher alcohol having 12 or more and 22 or less carbon atoms comprising (b1) cetanol and (b2) stearyl alcohol;

(C) 0.1 mass % or more and 10 mass % or less of a surfactant comprising one or more selected from the group consisting of (c1) a nonionic surfactant selected from the group consisting of sorbitan fatty acid ester and polyoxyethylene sorbitan fatty acid ester, and (c2) an anionic surfactant being a fatty acid having 12 or more and 22 or less carbon atoms or a salt thereof; and (D) water,
wherein a mass ratio of the content of (E) an oil agent other than ingredients (A), (B), and (C) and a flavoring agent to the content of ingredient (B), ((E)/(B)), is less than 1; and
the content of an abrasive powder (F) comprising a polyvalent metal is 5 mass % or less.

The medicinal ingredients such as glycyrrhetinic acid and tocopherol have a high risk of giving foreign taste and are also regulated by the Pharmaceutical Affairs Law in Japan, the amount thereof is accordingly limited. In order to sufficiently exert the effect of the medicinal ingredient under such circumstances, an increase in adsorption performance to the gums and oral mucosa is effective but has not been sufficiently investigated yet.

Accordingly, the present inventors found that when an oral composition comprises specific higher alcohol and surfactant in specific amounts, respectively, in addition to an oil-soluble medicinal ingredient, such as glycyrrhetinic acid, and water such that the content of oil agent other than the oil-soluble medicinal ingredient, higher alcohol, and flavoring agent is restricted with respect to the content of the higher alcohol and that the content of an abrasive powder comprising a polyvalent metal is restricted, the amount of the oil-soluble medicinal ingredient adsorbed to the gums and oral mucosa can be effectively increased.

According to the oral composition of the present invention, α-gel having a lamellar structure is formed to enhance the adsorption performance while effectively embedding the oil-soluble medicinal ingredient, and the amount adsorbed to the gums and oral mucosa can be effectively increased. Accordingly, the medicinal effects of the oil-soluble medicinal ingredient can also be sufficiently exerted. In addition, the oral composition of the present invention is also extremely useful as an agent for promoting adsorption of the oil-soluble medicinal ingredient to the gums and oral mucosa.

DETAILED DESCRIPTION OF THE INVENTION

The present invention will now be described in detail.

The oral composition of the present invention comprises 0.01 mass % or more and 1.5 mass % or less of one or more oil-soluble medicinal ingredients selected from the group consisting of glycyrrhetinic acid, tocopherol, and a tocopherol derivative as ingredient (A). Consequently, for example, anti-inflammatory action, alveolar bone resorption suppressing action, histamine release inhibiting action, and blood circulation promoting action can be provided, and action of preventing or improving, for example, periodontitis and periodontal disease can also be provided.

Examples of the glycyrrhetinic acid include α-glycyrrhetinic acid, β-glycyrrhetinic acid, and glycyrrhizic acid. In particular, β-glycyrrhetinic acid is preferred. Examples of the tocopherol and a derivative thereof include tocopherol acetate, tocopherol succinate, and tocopherol nicotinate. Among these examples, tocopherol acetate is preferred, and DL-α-tocopherol acetate is more preferred. In the present invention, one or more selected from the group consisting of these examples of glycyrrhetinic acid, tocopherol, and tocopherol derivative can be used.

The content of ingredient (A) in the oral composition of the present invention is 0.01 mass % or more, preferably 0.02 mass % or more, more preferably 0.05 mass % or more, even more preferably 0.08 mass % or more from the viewpoint of effectively exerting a desired pharmacological effect. The content of ingredient (A) in the oral composition of the present invention is 2.5 mass % or less, preferably 2.3 mass % or less, more preferably 1.5 mass % or less, even more preferably 1 mass % or less, further preferably 0.5 mass % or less, further more preferably 0.3 mass % or less, from the viewpoint of ensuring good flavor. The content of ingredient (A) in the oral composition of the present invention is 0.01 mass % or more and 2.5 mass % or less, preferably from 0.02 to 2.3 mass %, more preferably from 0.05 to 2.3 mass %, even more preferably from 0.08 to 2.3 mass %, further preferably from 0.08 to 1.5 mass %, further more preferably from 0.08 to 1 mass %, further more preferably from 0.08 to 0.5 mass %, further more preferably from 0.08 to 0.3 mass %.

It is particularly preferred that a glycyrrhetinic acid is included as ingredient (A), and the content of glycyrrhetinic acid in the oral composition of the present invention is preferably 0.01 mass % or more, more preferably 0.02 mass % or more, even more preferably 0.05 mass % or more, further preferably 0.08 mass % or more and preferably 0.5 mass % or less, more preferably 0.3 mass % or less.

The oral composition of the present invention comprises 4 mass % or more and 30 mass % or less of a higher alcohol having 12 or more and 22 or less carbon atoms comprising (b1) cetanol and (b2) stearyl alcohol as ingredient (B). That is, ingredient (B) is a higher alcohol having 12 or more and 22 or less carbon atoms including, as essential ingredients, cetanol as ingredient (b1) and stearyl alcohol as ingredient (b2). Such ingredient (B), together with ingredient (A) described above and ingredient (C) described below, forms α-gel having a structure in which lamellar layers pile up and can effectively increase the adsorption performance of ingredient (A) to the gums and oral mucosa while suitably embedding ingredient (A).

From the viewpoint of maintaining an appropriate viscosity as an oral composition while suitably forming α-gel, the higher alcohol as ingredient (B) is a higher alcohol including cetanol as ingredient (b1) and stearyl alcohol as ingredient (b2) and has 12 or more and 22 or less carbon atoms, wherein the mass ratio of the sum of the content of ingredient (b1) and the content of ingredient (b2) to the content of ingredient (B), (((b1)+(b2))/(B)), is preferably 0.85 or more, more preferably 0.9 or more, even more preferably 0.92 or more and preferably 1 or less.

Ingredient (B) other than ingredient (b1) and ingredient (b2) is preferably one or more selected from the group consisting of lauryl alcohol, myristyl alcohol, and behenyl alcohol.

The mass ratio of the content of ingredient (b1) to the content of ingredient (b2), ((b1)/(b2)), is preferably 0.5 or more, more preferably 0.7 or more and preferably 5 or less, more preferably 3 or less, even more preferably 2 or less, further preferably 1.7 or less, from the viewpoint of enhancing the stability as an oral composition while satisfactorily forming α-gel.

Lauryl alcohol and myristyl alcohol, which are higher alcohols having 12 or more and 22 or less carbon atoms other than ingredient (b1) and ingredient (b2), may be contained such that the mass ratio of the sum of the content of lauryl alcohol and the content of myristyl alcohol to the content of ingredient (B), ((lauryl alcohol+myristyl alcohol)/(B)), is preferably 0.05 or less, more preferably 0.03 or less, even more preferably 0.01 or less, from the viewpoint of taste.

Behenyl alcohol, which is a higher alcohol having 12 or more and 22 or less carbon atoms other than ingredient (b1) and ingredient (b2), may be contained such that the mass ratio of the content of behenyl alcohol to the content of ingredient (B), (behenyl alcohol/(B)), is preferably 0.1 or less, more preferably 0.05 or less, from the viewpoint of preventing precipitation and separation of ingredient (B).

A higher alcohol having 10 or less carbon atoms may be contained such that the mass ratio of the content of the higher alcohol having 10 or less carbon atoms to the content of ingredient (B), (higher alcohol having 10 or less carbon atoms/(B)), is preferably 0.1 or less, more preferably 0.01 or less, even more preferably 0.005 or less, from the viewpoint of stability. Alternatively, the oral composition of the present invention further preferably does not contain a higher alcohol having 10 or less carbon atoms.

A higher alcohol having 24 or more carbon atoms may be contained such that the mass ratio of the content of the higher alcohol having 24 or more carbon atoms to the content of ingredient (B), (higher alcohol having 24 or more carbon atoms/(B)), is preferably 0.1 or less, more preferably 0.01 or less, even more preferably 0.005 or less, from the viewpoint of stability. Alternatively, the oral composition of the present invention further preferably does not contain a higher alcohol having 24 or more carbon atoms.

The content of ingredient (B) in the oral composition of the present invention is 4 mass % or more, preferably 4.5 mass % or more from the viewpoint of satisfactorily forming α-gel. The content of ingredient (B) in the oral composition of the present invention is 30 mass % or less, preferably 25 mass % or less, more preferably 20 mass % or less, even more preferably 18 mass % or less from the viewpoint of an appropriate viscosity and the viewpoint of ensuring the dispersibility of each ingredient in the composition. The content of ingredient (B) in the oral composition of the present invention is 4 mass % or more and 30 mass % or less, preferably from 4 to 25 mass %, more preferably from 4 to 20 mass %, even more preferably from 4.5 to 18 mass %.

The mass ratio of the content of ingredient (A) to the content of ingredient (B), ((A)/(B)), is preferably 0.002 or more, more preferably 0.004 or more, more preferably 0.005 or more from the viewpoint of satisfactorily embedding ingredient (A) in α-gel formed while ensuring the pharmacological effect of ingredient (A). Also, the mass ratio of the content of ingredient (A) to the content of ingredient (B), ((A)/(B)), is preferably 0.5 or less, more preferably 0.4 or less, even more preferably 0.3 or less, further preferably 0.2 or less, further more preferably 0.15 or less from the viewpoint of increasing the adsorption performance of ingredient (A) to the gums and oral mucosa while ensuring the dispersibility of each ingredient. When a glycyrrhetinic acid is included as ingredient (A), the mass ratio of the content of the glycyrrhetinic acid to the content of ingredient (B), (glycyrrhetinic acid/(B)), is preferably 0.1 or less, more preferably 0.075 or less, and even more preferably 0.05 or less. Also, the mass ratio of the content of ingredient (A) to the content of ingredient (B), ((A)/(B)), is preferably from 0.002 to 0.5, more preferably from 0.004 to 0.4, even more preferably from 0.005 to 0.3, further preferably from 0.005 to 0.2, further more preferably from 0.005 to 0.15. When a glycyrrhetinic acid is included as ingredient (A), the mass ratio of the content of the glycyrrhetinic acid to the content of ingredient (B), (glycyrrhetinic acid/(B)), is preferably from 0.002 to 0.1, more preferably from 0.004 to 0.075, even more preferably from 0.005 to 0.05.

The oral composition of the present invention comprises, as ingredient (C), 0.1 mass % or more and 10 mass % or less of a surfactant comprising one or more selected from the group consisting of (C1) a nonionic surfactant selected from the group consisting of sorbitan fatty acid ester and polyoxyethylene sorbitan fatty acid ester, and (c2) an anionic surfactant being a fatty acid salt having 12 or more and 22 or less carbon atoms. Thus, use of a specific amount of the surfactant as ingredient (C) comprising one or more selected from the group consisting of the nonionic surfactant as ingredient (c1) and the anionic surfactant as ingredient (c2) can form, together with ingredient (B), α-gel to further satisfactorily embed ingredient (A) while ensuring the stability of the ingredient (A) and can effectively increase the adsorption performance of ingredient (A) to the gums and oral mucosa.

Ingredient (c1) is a nonionic surfactant selected from the group consisting of sorbitan fatty acid ester and polyoxyethylene sorbitan fatty acid ester. The sorbitan fatty acid ester is, for example, one or more selected from preferably those derived from a fatty acid having 10 or more carbon atoms, more preferably those derived from a fatty acid having 12 or more carbon atoms, and preferably those derived from a fatty acid having 20 or less carbon atoms, more preferably those derived from a fatty acid having 18 or less carbon atoms, from the viewpoint of the adsorption performance of ingredient (A) to the gums and oral mucosa. Specifically, for example, the sorbitan fatty acid ester is one or more selected from the group consisting of sorbitan monocaprylate, sorbitan monoundecylate, sorbitan monolaurate, sorbitan monotridecylate, sorbitan monomyristate, sorbitan monopalmitate, sorbitan monooleate, sorbitan trioleate, sorbitan tetraoleate, sorbitan sesquioleate, sorbitan monostearate, sorbitan tristearate, and so on. Among these examples, preferred are one or more selected from the group consisting of sorbitan monooleate, sorbitan sesquioleate, sorbitan monostearate, and sorbitan monopalmitate; and more preferred are one or more selected from the group consisting of sorbitan monooleate, sorbitan sesquioleate, and sorbitan monostearate.

The polyoxyethylene sorbitan fatty acid ester is, for example, one or more selected from preferably those derived from a fatty acid having 6 or more carbon atoms, more preferably those derived from a fatty acid having 12 or more carbon atoms, and preferably those derived from a fatty acid having 22 or less carbon atoms, more preferably those derived from a fatty acid having 20 or less carbon atoms, from the viewpoint of the adsorption performance of ingredient (A) to the gums and oral mucosa. Also, the average molar number of the added ethyleneoxy group in the polyoxyethylene sorbitan fatty acid ester is, from the same viewpoint, preferably from 5 to 40 moles, more preferably from 10 to 25 moles, even more preferably from 10 to 20 moles. Such a polyoxyethylene sorbitan fatty acid ester is, for example, one or more selected from the group consisting of polyoxyethylene sorbitan monolaurate, polyoxyethylene sorbitan monomyristate, polyoxyethylene sorbitan monopalmitate, polyoxyethylene sorbitan monostearate, and polyoxyethylene sorbitan monooleate. Among these examples, preferred are one or more selected from the group consisting of polyoxyethylene sorbitan monopalmitate, polyoxyethylene sorbitan monostearate, and polyoxyethylene sorbitan monooleate, from the viewpoint of enhancing low-temperature stability while showing excellent foamability.

The anionic surfactant as ingredient (c2) is a fatty acid having 12 or more and 22 or less carbon atoms or a salt thereof. Ingredient (c2) has 12 or more carbon atoms, preferably 14 or more carbon atoms, more preferably 16 or more carbon atoms and 22 or less carbon atoms, preferably 20 or less carbon atoms, more preferably 18 or less carbon atoms, from the viewpoint of the adsorption performance of ingredient (A) to the gums and oral mucosa and the viewpoint of ensuring good flavor. The fatty acid constituting ingredient (c2) may be a linear chain or may be a branched chain, the fatty acid is preferably a linear chain from the viewpoint of the adsorption performance of ingredient (A) to the gums and oral mucosa. Specifically, such ingredient (c2) is, for example, one or more selected from the group consisting of lauric acid, myristic acid, palmitic acid, stearic acid, coconut oil fatty acid, and salts thereof. Among these examples, preferred are one or more selected from the group consisting of myristic acid, palmitic acid, stearic acid, and salts thereof; and it is more preferred that stearic acid or a salt thereof is at least included as ingredient (c2). Examples of the salt constituting ingredient (c2) include alkali metals selected from the group consisting of sodium and potassium; basic amino acids such as arginine; alkanolammoniums such as monoethanolammonium, diethanolammonium, and triethanolammonium; and ammonium. Among these examples, the salt constituting ingredient (c2) is preferably an alkali metal selected from the group consisting of sodium and potassium from the viewpoint of stability.

Ingredient (C) comprises one or more selected from the group consisting of the above-mentioned ingredient (c1) and ingredient (c2) and may further comprise one or more selected from the group consisting of (c3) a nonionic surfactant selected from the group consisting of polyoxyethylene hydrogenated castor oil, sucrose fatty acid ester, and polyglycerin fatty acid ester, and (c4) an anionic surfactant selected from the group consisting of sodium alkylsulfate, an acyl methyl taurine salt, and an acyl sarcosine salt. That is, the oral composition of the present invention comprises one or more selected from a nonionic surfactant of ingredient (c1) and an anionic surfactant of ingredient (c2) as the surfactant of ingredient (C), and can further comprise ingredient (c3) as a nonionic surfactant other than ingredient (c1), or ingredient (c4) as an anionic surfactant other than ingredient (c2).

The average molar number of the added ethyleneoxy group in the polyoxyethylene hydrogenated castor oil as ingredient (c3) is preferably from 20 to 100 moles, more preferably from 40 to 80 moles, from the viewpoint of ensuring the stability of the composition while satisfactorily maintaining the adsorption performance of ingredient (A) to the gums and oral mucosa. The content of the polyoxyethylene hydrogenated castor oil of ingredient (c3) in the oral composition of the present invention is preferably 0.5 mass % or less, more preferably 0.3 mass % or less, even more preferably 0.1 mass % or less, further preferably 0.01 mass % or less from the viewpoint of satisfactorily maintaining the adsorption performance of ingredient (A) to the gums or oral mucosa. Alternatively, the oral composition of the present invention need not contain polyoxyethylene hydrogenated castor oil.

Examples of the polyglycerin fatty acid ester of ingredient (c3) include those in which one to four fatty acid molecules having 8 to 24 carbon atoms are ester-bonded to polyglycerin composed of 2 to 20 condensed glycerin molecules. The fatty acid moiety constituting the polyglycerin fatty acid ester is preferably derived from a fatty acid having 12 to 20 carbon atoms, more preferably derived from a fatty acid having 12 to 18 carbon atoms, even more preferably derived from a fatty acid having 12 to 14 carbon atoms, from the viewpoint of ensuring the stability of the composition while satisfactorily maintaining the adsorption performance of ingredient (A) to the gums and oral mucosa, and the polyglycerin fatty acid ester is preferably a monoester composed of these fatty acid moieties. The average degree of condensation of glycerin in the polyglycerin fatty acid ester is, from the same viewpoint, preferably 2 to 20, more preferably 5 to 12.

Examples of the sucrose fatty acid ester of ingredient (c3) include sucrose fatty acid ester composed of fatty acid moiety derived from a fatty acid having 6 to 20 carbon atoms. Among these examples, the fatty acid moiety constituting the sucrose fatty acid ester is preferably derived from a fatty acid having 10 to 18 carbon atoms and more preferably derived from a fatty acid having 12 to 14 carbon atoms, from the viewpoint of ensuring the stability of the composition while satisfactorily maintaining the adsorption performance of ingredient (A) to the gums and oral mucosa and the viewpoint of providing good feel upon use.

Examples of ingredient (c4), one or more anionic surfactants selected from the group consisting of an alkyl sulfate, an acyl methyl taurine salt, and an acyl sarcosine salt include, for example, one or more selected from an alkyl sulfate such as sodium lauryl sulfate and sodium myristyl sulfate; sodium or potassium salts of acyl sarcosine such as N-lauroyl sarcosine, N-myristoyl sarcosine, N-palmitoyl sarcosine, N-stearoyl sarcosine, N-isostearoyl sarcosine, and N-oleoyl sarcosine; and sodium or potassium salts of acyl methyl taurine such as capryl methyl taurine, lauryl methyl taurine, myristyl methyl taurine, palmityl methyl taurine, and stearyl methyl taurine. Among these examples, preferred are one or more selected from the group consisting of sodium lauryl sulfate, an N-lauroylsarcosine salt, an N-myristoylsarcosine salt, a lauryl methyl taurine salt, and a myristyl methyl taurine salt; and more preferred is sodium lauryl sulfate.

The content of ingredient (c1) in the oral composition of the present invention is preferably 0.2 mass % or more, more preferably 0.4 mass % or more, even more preferably 0.5 mass % or more from the viewpoint of forming, together with ingredient (B), α-gel to further satisfactorily embed ingredient (A) while ensuring the stability of ingredient (A) and effectively increasing the adsorption performance of ingredient (A) to the gums and oral mucosa, and is 10 mass % or less, preferably 8 mass % or less, more preferably 6 mass % or less from the viewpoint of ensuring the stability of the composition and the viewpoint of appropriate balance with the viscosity and flavor.

When ingredient (c2) is not contained, the content of ingredient (c1) in the oral composition of the present invention is preferably 1 mass % or more, more preferably 1.5 mass % or more, even more preferably 2 mass % or more from the viewpoint of forming, together with ingredient (B), α-gel to further satisfactorily embed ingredient (A) while ensuring the stability of ingredient (A) and effectively increasing the adsorption performance of ingredient (A) to the gums and oral mucosa.

When ingredient (c2) is contained, the content of ingredient (c1) in the oral composition is preferably 5 mass % or less.

The content of ingredient (c2) in the oral composition of the present invention is preferably 0.05 mass % or more, more preferably 0.08 mass % or more, even more preferably 0.1 mass % or more in terms of fatty acids from the viewpoint of forming, together with ingredient (B), α-gel to further satisfactorily embed ingredient (A) while ensuring the stability of ingredient (A) and effectively increasing the adsorption performance of ingredient (A) to the gums and oral mucosa and the viewpoint of providing an appropriate viscosity; further more preferably 0.2 mass % or more from the viewpoint of forming, together with ingredient (B), α-gel and providing an appropriate viscosity; further more preferably 1 mass % or more from the viewpoint of providing a viscosity showing shape-retainability and high adsorption property. The content of ingredient (c2) in the oral composition of the present invention is preferably 5 mass % or less, more preferably 3 mass % or less, even more preferably 2.5 mass % or less, further preferably 2 mass % or less in terms of fatty acids from the viewpoint of ensuring the stability of the composition, the viewpoint of appropriate balance with the viscosity and flavor, and the viewpoint of reducing harm on the oral mucosa, further more preferably 0.5 mass % or less, further more preferably 0.2 mass % or less from the viewpoint of more excellent flavor.

The sum of the content of ingredient (c1) and the content of ingredient (c2) in terms of fatty acids in the oral composition of the present invention is preferably 0.1 mass % or more, more preferably 0.2 mass % or more, even more preferably 0.3 mass % or more, further more preferably 0.4 mass % or more, further more preferably 0.5 mass % or more from the viewpoint of forming, together with ingredient (B), α-gel to further satisfactorily embed ingredient (A) while ensuring the stability of ingredient (A) and effectively increasing the adsorption performance of ingredient (A) to the gums and oral mucosa and is preferably 10 mass % or less, more preferably 8 mass % or less, even more preferably 6.5 mass % or less from the viewpoint of ensuring the stability of the composition and the viewpoint of appropriate balance with the viscosity and flavor. The oral composition of the present invention preferably comprises both ingredient (c1) and ingredient (c2).

The content of ingredient (c3) in the oral composition of the present invention is preferably 0.5 mass % or less, more preferably 0.25 mass % or less, even more preferably 0.2 mass % or less, further more preferably 0.1 mass % or less, further more preferably 0.05 mass % or less from the viewpoint of increasing the adsorption performance of ingredient (A) to the gums and oral mucosa and the viewpoint of ensuring balance between the adsorption performance of ingredient (A) to the gums and oral mucosa and flavor.

The content of ingredient (c4) in the oral composition of the present invention is preferably 2 mass % or less, more preferably 1.5 mass % or less, even more preferably 1 mass % or less, further preferably 0.7 mass % or less from the viewpoint of harm on the gums and oral mucosa and flavor.

The content of ingredient (C) in the oral composition of the present invention is 0.1 mass % or more, preferably 0.2 mass % or more, more preferably 0.3 mass % or more, even more preferably 0.4 mass % or more, further more preferably 0.5 mass % or more from the viewpoint of forming, together with ingredient (B), α-gel to further satisfactorily embed ingredient (A) while ensuring the stability of ingredient (A) and effectively increasing the adsorption performance of ingredient (A) to the gums and oral mucosa. The content of ingredient (C) in the oral composition of the present invention is 10 mass % or less, preferably 9 mass % or less, more preferably 8 mass % or less, even more preferably 7 mass % or less from the viewpoint of ensuring the stability of the composition and the viewpoint of appropriate balance with the viscosity and flavor. The content of ingredient (C) in the oral composition of the present invention is 0.1 mass % or more and 10 mass % or less, preferably from 0.2 to 9 mass %, more preferably from 0.3 to 8 mass %, even more preferably from 0.4 to 7 mass %.

When the oral composition of the present invention comprises ingredient (c1) as ingredient (C), the mass ratio of the content of ingredient (B) to the content of the nonionic surfactant including ingredient (c1), ((B)/nonionic surfactant), is preferably 1 or more, more preferably 1.2 or more, even more preferably 1.4 or more from the viewpoint of satisfactorily forming α-gel and increasing the adsorption performance of ingredient (A) to the gums and oral mucosa. The mass ratio of the content of ingredient (B) to the content of the nonionic surfactant including ingredient (c1), ((B)/ nonionic surfactant), is preferably 20 or less, more preferably 17 or less, even more preferably 15 or less from the viewpoint of maintaining an appropriate viscosity as an oral composition and the viewpoint of stability, and the mass ratio when ingredient (c2) is not contained as ingredient (C) is preferably 10 or less, more preferably 5 or less, even more preferably 3.5 or less. The mass ratio of the content of ingredient (B) to the content of the nonionic surfactant including ingredient (c1), ((B)/nonionic surfactant), is preferably from 1 to 20, more preferably from 1.2 to 17, even more preferably from 1.4 to 15. The mass ratio when ingredient (c2) is not contained as ingredient (C) is preferably from 1 to 10, more preferably from 1.2 to 5, even more preferably from 1.4 to 3.5.

When the oral composition of the present invention comprises ingredient (c2) as ingredient (C), the mass ratio of the content of ingredient (B) to the content of the anionic surfactant including ingredient (c2), ((B)/anionic surfactant), is preferably 3 or more, more preferably 4 or more, even more preferably 5 or more, further preferably 7 or more, further more preferably 10 or more from the viewpoint of satisfactorily forming α-gel and increasing the adsorption performance of ingredient (A) to the gums and oral mucosa. The mass ratio of the content of ingredient (B) to the content of the anionic surfactant including ingredient (c2), ((B)/anionic surfactant), is preferably 200 or less, more preferably 180 or less from the viewpoint of ensuring stability while maintaining an appropriate viscosity as an oral composition and the viewpoint of providing good feel upon use, and is even more preferably 90 or less, further preferably 18 or less from the viewpoint of increasing the adsorption performance of ingredient (A) to the gums and oral mucosa while ensuring a high viscosity. The mass ratio of the content of ingredient (B) to the content of the anionic surfactant including ingredient (c2), ((B)/anionic surfactant), is preferably from 3 to 200, more preferably from 5 to 200, even more preferably from 5 to 180, further preferably from 7 to 180, further more preferably from 10 to 180 and is preferably from 3 to 180, more preferably from 3 to 90, even more preferably from 4 to 18 from the viewpoint of increasing the adsorption performance of ingredient (A) to the gums and oral mucosa while ensuring a high viscosity.

In the oral composition of the present invention, the mass ratio of the content of ingredient (B) to the sum of the content of ingredient (c1) and the content of ingredient (c2) in terms of fatty acids, ((B)/((c1)+(c2))), is preferably higher than 1, more preferably 1.2 or more, even more preferably 1.5 or more from the viewpoint of satisfactorily forming α-gel and increasing the adsorption performance of ingredient (A) to the gums and oral mucosa. The mass ratio of the content of ingredient (B) to the sum of the content of ingredient (c1) and the content of ingredient (c2) in terms of fatty acids, ((B)/((c1)+(c2))), is preferably 40 or less, more preferably 35 or less, even more preferably 30 or less from the viewpoint of ensuring stability while maintaining an appropriate viscosity as an oral composition and the viewpoint of providing good feel upon use. The mass ratio of the content of ingredient (B) to the sum of the content of ingredient (c1) and the content of ingredient (c2) in the terms of fatty acids, ((B)/((c1)+(c2))), is preferably more than 1 and 40 or less, more preferably from 1.2 to 35, even more preferably from 1.5 to 30.

It is preferred to restrict inclusion of a cationic surfactant other than the cationic bactericide in the oral composition of the present invention from the viewpoint of preventing harm on the oral mucosa. The content of the cationic surfactant other than the cationic bactericide in the oral composition of the present invention is preferably 0.1 mass % or less, more preferably 0.05 mass % or less, even more preferably 0.01 mass % or less. Alternatively, the oral composition of the present invention preferably does not contain a cationic surfactant other than the cationic bactericide. The cationic bactericide is, for example, one or more selected from the group consisting of quaternary ammonium compounds and biguanide compounds. Examples of the quaternary ammonium compound include cetyl pyridinium chloride, benzethonium chloride, benzalkonium chloride, stearyl dimethyl ammonium chloride, stearyl trimethyl ammonium chloride, cetyl trimethyl ammonium chloride, methyl benzethonium chloride, lauryl trimethyl ammonium chloride, and lauroyl colamino formyl methyl pyridinium chloride. Examples of the biguanide compound include chlorhexidine and its salts such as chlorhexidine gluconate and chlorhexidine chlorate.

The oral composition of the present invention preferably comprises a cationic bactericide from the viewpoint of increasing the adsorption performance of ingredient (A) to the gums and oral mucosa in the presence of α-gel in the composition. In particular, the cationic bactericide is preferably a quaternary ammonium compound selected from the group consisting of cetyl pyridinium chloride, benzethonium chloride, benzalkonium chloride, stearyl dimethyl ammonium chloride, stearyl trimethyl ammonium chloride, cetyl trimethyl ammonium chloride, methyl benzethonium chloride, lauryl trimethyl ammonium chloride, and lauroyl colamino formyl methyl pyridinium chloride from the viewpoint of increasing the adsorption performance of the ingredient (A) to the gums and oral mucosa; more preferably one or more selected from the group consisting of cetyl pyridinium chloride, benzethonium chloride, and benzalkonium chloride from the viewpoint of sterilization performance; even more preferably cetyl pyridinium chloride.

The content of the cationic bactericide in the oral composition of the present invention is preferably 0.005 mass % or more, more preferably 0.01 mass % or more, even more preferably 0.02 mass % or more from the viewpoint of increasing the adsorption performance of ingredient (A) to the gums and oral mucosa and is preferably 0.1 mass % or less, more preferably 0.08 mass % or less, even more preferably 0.06 mass % or less from the viewpoint of flavor and irritation.

In the oral composition of the present invention, the mass ratio of the content of the cationic bactericide to the content of ingredient (B), (cationic bactericide/ingredient (B)), is preferably 0.001 or more, more preferably 0.002 or more and preferably 0.02 or less, more preferably 0.01 or less from the viewpoint of satisfactorily forming α-gel and increasing the adsorption performance of ingredient (A) to the gums and oral mucosa.

In the oral composition of the present invention, the mass ratio of the content of the cationic bactericide to the content of a glycyrrhetinic acid, (cationic bactericide/glycyrrhetinic acid), is preferably 0.01 or more, more preferably 0.05 or more, even more preferably 0.1 or more and preferably 2 or less, more preferably 1.5 or less, even more preferably 1 or less, further preferably 0.8 or less from the viewpoint of increasing the adsorption performance of the glycyrrhetinic acid to the gums and oral mucosa.

The oral composition of the present invention comprises water as ingredient (D). The term "water" of ingredient (D) in the present invention refers to the total water in the oral composition comprising not only, for example, purified water blended to the oral composition but also the water contained in each of the blended ingredients, such as a 70% sorbitol liquid (aqueous solution) and a 48% potassium hydroxide liquid (aqueous solution) used in formulation. The oral composition thus-comprising water as ingredient (D) can satisfactorily disperse or dissolve each ingredient and improve the good feel upon use and the adsorption performance of ingredient (A) to the gums or oral mucosa, while ensuring an appropriate viscosity and good shape-retainability as an oral composition and satisfactorily maintaining the formed α-gel in the composition. The content of ingredient (D) in the oral composition of the present invention is preferably 30 mass % or more, more preferably 40 mass % or more, even more preferably 50 mass % or more, more preferably 55 mass % or more and preferably 95 mass % or less, more preferably 92 mass % or less. The content of ingredient (D) in the oral composition of the present invention is preferably from 30 to 95 mass %, more preferably from 40 to 92 mass %, even more preferably from 50 to 92 mass %, further preferably from 55 to 92 mass %.

The content of ingredient (D), i.e., the water content in the oral composition of the present invention can be calculated from the content of the blended water and the content of water in the blended ingredients, and the content can also be measured with, for example, a Karl Fischer moisture meter. As the Karl Fischer moisture meter, for example, a trace moisture measuring device (Hiranuma Sangyo Co., Ltd.) can be used. In this device, 5 g of an oral composition is suspended in 25 g of anhydrous methanol, and the water content in 0.02 g of this suspension can be measured.

In the oral composition of the present invention, the mass ratio of the content of an oil agent (E) other than ingredients (A), (B), and (C) and the flavoring agent to the content of ingredient (B), ((E)/(B)), is less than 1. In the oral composition of the present invention, the restriction of the content of the oil agent (E) with respect to the content of ingredient (B) can improve the stability of the oral composition within the limited range of the surfactant that can be blended in the composition, can effectively prevent inhibition of α-gel formation by ingredients (A) to (C), and can provide good flavor. Examples of ingredient (E) include hydrocarbon oils, such as liquid paraffin, vaseline, mineral oil, light liquid paraffin, paraffin wax, ceresin, microcrystalline wax, carnauba wax, bees wax, squalane, and squalene; ester oils, such as isopropyl myristate, isopropyl palmitate, propyl adipate, diethyl sebacate, and glycerin fatty acid ester; triglycerides and vegetable oils containing it, such as olive oil, rapeseed oil, shea butter, and rice bran oil; silicone oil; preservatives, such as methyl parahydroxybenzoate and ethyl parahydroxybenzoate; and oil-soluble bactericides.

The mass ratio of the content of ingredient (E) to the content of ingredient (B), ((E)/(B)), is less than 1, preferably 0.5 or less, more preferably 0.3 or less.

The content of ingredient (E) in the oral composition of the present invention is preferably 5 mass % or less, more preferably 2 mass % or less, even more preferably 1 mass % or less, further preferably 0.5 mass % or less. When ingredient (E) is an oil agent that is a liquid at 25° C., the content of ingredient (E) in the oral composition of the present invention is preferably 5 mass % or less, more preferably 3 mass % or less, even more preferably 2 mass % or less.

In the oral composition of the present invention, the content of an abrasive (F) (abrasive powder) comprising a polyvalent metal is 5 mass % or less. It is consequently possible to prevent the α-gel formed by ingredients (A) to (C) from collapsing. In particular, when ingredient (c2) is contained, it is possible to prevent precipitation of a metal salt due to bonding of ingredient (c2) and the polyvalent metal as ingredient (F), and excellent adsorption performance of ingredient (A) to the gums or oral mucosa can be ensured. Examples of the polyvalent metal include aluminum, calcium, zirconium, iron, copper, zinc, and manganese. Examples of ingredient (F) comprising the polyvalent metal include water-insoluble calcium compounds, such as calcium carbonate; calcium hydrogen phosphate; insoluble potassium metaphosphate; aluminum silicate; zirconium silicate; aluminum oxide; aluminum hydroxide; and zinc oxide. The content of ingredient (F) in the oral composition of the present invention is 5 mass % or less, preferably 3 mass % or less, more preferably 1 mass % or less. Alternatively, the oral composition of the present invention preferably does not contain ingredient (F) excluding the case when it is inevitably contaminated.

In the oral composition of the present invention, from the same viewpoint, the content of the polyvalent metal selected from the group consisting of strontium, magnesium, aluminum, calcium, zirconium, iron, copper, zinc, and manganese is preferably 2 mass % or less, more preferably 1 mass % or less, even more preferably 0.5 mass % or less, further preferably 0.1 mass % or less in terms of metal atom in the oral composition of the present invention.

It is preferred to restrict inclusion of a cellulose binder in the oral composition of the present invention from the viewpoint of maintaining an appropriate viscosity and shape-retainability as an oral composition due to the formed α-gel and ensuring excellent adsorption performance of ingredient (A) to the gums or oral mucosa. Examples of the cellulose binder include sodium carboxymethyl cellulose and hydroxyalkyl cellulose (e.g., hydroxyethyl cellulose and hydroxypropyl cellulose). The content of the cellulose binder in the oral composition of the present invention is preferably 0.3 mass % or less, more preferably 0.25 mass % or less, even more preferably 0.2 mass % or less, further preferably 0.1 mass % or less. Alternatively, the oral composition of the present invention preferably does not contain a cellulose binder excluding the case when it is inevitably contaminated.

The oral composition of the present invention can comprise a binder other than the cellulose binder. The binder other than the cellulose binder is, for example, one or more selected from the group consisting of sodium alginate, carrageenan, xanthan gum, sodium polyacrylate, pectin, agar, gum tragacanth, gum arabic, guar gum, karaya gum, locust bean gum, gella gum, tamarid gum, *psyllium* seed gum, and carboxyvinyl polymers, and is preferably one or more selected from the group consisting of carrageenan and xanthan gum. As the carboxyvinyl polymer, commercially available products, such as Carbopol 940, 941 (Lubrizol Advanced Materials, Inc.), can be used.

The content of the binder other than the cellulose binder is preferably 0.5 mass % or less, more preferably 0.3 mass % or less, even more preferably 0.2 mass % or less from the viewpoint of enhancing the adsorption performance of ingredient (A) to the gums or oral mucosa. The content of the carboxyvinyl polymer is preferably 0.3 mass % or less, more preferably 0.2 mass % or less, even more preferably 0.1 mass % or less, further preferably 0.05 mass % or less, further more preferably 0.01 mass % or less from the viewpoint of further enhancing the adsorption performance of ingredient (A) to the gums or oral mucosa.

It is preferred that the oral composition of the present invention further comprises a thickener from the viewpoint of enhancing the viscoelasticity by the binder. The thickener is preferably one or more selected from thickening silica having an oil absorption of 180 to 350 mL/100 g and fatty acid dextrin. The content of the thickening silica in the oral composition of the present invention is preferably 5 mass % or less, more preferably 3 mass % or less from the viewpoint of increasing the adsorption performance of ingredient (A) to the gums or oral mucosa. The content of the fatty acid dextrin in the oral composition of the present invention is preferably 3 mass % or less, more preferably 1.5 mass % or less from the viewpoint of increasing the adsorption performance of ingredient (A) to the gums or oral mucosa and the viewpoint of balance with flavor. The fatty acid dextrin is preferably dextrin palmitate.

The oral composition of the present invention can comprise abrasive silica having an oil absorption of 50 to 150 mL/100 g. The abrasive silica is an abrasive other than the above-mentioned abrasive (abrasive powder) comprising a polyvalent metal. The content of the abrasive silica in the oral composition of the present invention is preferably 7 mass % or less, more preferably 5 mass % or less, even more preferably 3 mass % or less, further preferably 2 mass % or less, further more preferably 1 mass % or less from the viewpoint of increasing the adsorption performance of ingredient (A) to the gums or oral mucosa. Alternatively, the oral composition of the present invention need not contain the abrasive silica having an oil absorption of 50 to 150 mL/100 g.

The term "oil absorption" refers to the amount of oil that can be supported by silica and means the value defined by the amount of absorbed boiled linseed oil measured by a method according to JIS K5101-13-2 (established in 2004).

It is preferred to restrict inclusion of ethanol in the oral composition of the present invention from the viewpoint of effectively preventing the α-gel formed by ingredients (A) to (C) from collapsing and maintaining excellent adsorption performance of ingredient (A) to the gums or oral mucosa, the viewpoint of ensuring an appropriate viscosity, and the viewpoint of suppressing irritation. Specifically, the content of ethanol in the oral composition of the present invention is preferably 8 mass % or less, more preferably 5 mass % or less, even more preferably 2 mass % or less. Alternatively, the oral composition of the present invention preferably does not contain ethanol.

It is preferred that the oral composition of the present invention further comprises a sugar alcohol from the viewpoint of flavor. The content of the sugar alcohol is preferably 30 mass % or less, more preferably 20 mass % or less, even more preferably 15 mass % or less from the viewpoint of increasing the adsorption performance of ingredient (A) to the gums or oral mucosa, and is preferably 1 mass % or more, more preferably 2 mass % or more, even more preferably 5 mass % or more from the viewpoint of flavor. The sugar alcohol is preferably one or more selected from the group consisting of sorbitol, xylitol, erythritol, reduced palatinose, and mannitol, and more preferably one or more selected from the group consisting of sorbitol and xylitol from the viewpoint of high solubility in water and providing a smooth feel to the composition. The composition preferably at least comprises sorbitol as the sugar alcohol.

The oral composition of the present invention can comprise, in addition to the above-mentioned ingredients, for example, a polyhydric alcohol, a sweetener, a humectant, a preservative, a fluoride, an enzyme, and a dye within a range not impairing the advantageous effects of the present invention.

The viscosity at 20° C. of the oral composition of the present invention is preferably 5,000 dPa·s or less, more preferably 4,000 dPa·s or less, even more preferably 3,800 dPa·s or less and preferably 300 dPa·s or more, more preferably 400 dPa·s or more, even more preferably 500 dPa·s or more, further preferably 700 dPa·s or more from the viewpoint of maintaining an appropriate viscosity and exerting excellent adsorption performance of ingredient (A) to the gums or oral mucosa and the viewpoint of ensuring good shape-retainability and feel upon use. The viscosity at 20° C. of the oral composition of the present invention is preferably 5,000 dPa·s or less, more preferably from 300 to 5,000 dPa·s, even more preferably from 400 to 4,000 dPa·s, further preferably from 500 to 3,500 dPa·s, further more preferably from 700 to 3,500 dPa·s. Such a viscosity can be measured using a composition packed in a container for viscosity measurement and preserved in an incubator of 20° C. for 24 hours with a Helipath viscometer (VISCOMETER TVB-10, Toki Sangyo Co., Ltd.) and a rotor T-C at a speed of 2.5 rpm for 1 minute.

Examples of the form of the oral composition of the present invention include toothpaste, a coating agent, a mouth wash, and a liquid dentifrice. Among these examples, a liquid dentifrice and toothpaste are preferred from the viewpoint of sufficiently supplying the oral composition of the present invention to the gums or oral mucosa and allowing effective adsorption of ingredient (A). The oral composition of the present invention is preferably used by applying the composition to the oral cavity and, after the application, rinsing the oral cavity with water. Even if the oral cavity is rinsed with water after the application, ingredient (A) can be effectively adsorbed to the gums or oral mucosa. The method for application to the oral cavity may be coating, brushing with a toothbrush, or gargling, and coating or brushing with a toothbrush is preferred.

The method of producing the oral composition of the present invention comprises a step of mixing a mixture liquid containing ingredient (B) and ingredient (C) at a temperature not lower than the melting point of ingredient (B) and not higher than 90° C. Specifically, a production method comprising the following step (X) is preferred from the viewpoint of effectively increasing the adsorption performance of ingredient (A) to the gums or oral mucosa, or a production method comprising the following step (Y) is preferred from the viewpoint of effectively increasing the adsorption performance of ingredient (A) to the gums or oral mucosa and the viewpoint of simplifying the production facilities.

In the production method comprising the step (X), the method comprises the step (X) in which a mixture liquid 1-1 containing ingredient (B) and ingredient (C) is mixed at a temperature not lower than the melting point of ingredient (B) and not higher than 90° C., and ingredient (D) is then added to and mixed with the resulting mixture liquid 1-1 to prepare a mixture liquid 1-2. In this production method, ingredient (A) is preferably included in the mixture liquid 1-1, and ingredient (A) may be, together with other ingredients such as a flavoring agent, added to and mixed with the mixture liquid 1-2 prepared through the step (X). Ingredient (D) may be partially mixed with the mixture liquid 1-1. When ingredient (C) contains ingredient (c2), it is preferred to mix a part of ingredient (D) with the mixture liquid 1-1. The temperature when the mixture liquid 1-1 is mixed may be a temperature not lower than the melting point of ingredient (B) and not higher than 90° C. and is a temperature not lower than the melting point that is the highest in ingredient (B), more preferably a temperature not lower than the melting point of ingredient (B) and not higher than 85° C., even more preferably a temperature not lower than 80° C. and not higher than 85° C. The order of mixing ingredients (A) to (C) is not particularly limited. The temperature not lower than the melting point of ingredient (B) is preferably 65° C. or more, more preferably 75° C. or more, even more preferably 80° C. or more.

In the production method comprising the step (Y), the method comprises the step (Y) in which a mixture liquid 2 containing ingredients (B) to (D) is mixed. In this production method, ingredient (A) is preferably included in the mixture liquid 2, and ingredient (A) may be, together with other ingredients such as a flavoring agent, added to and mixed with the mixture liquid 2 prepared through the step (Y).

The oral composition of the present invention can achieve effective adsorption of ingredient (A) to the gums or oral mucosa and, therefore, is also very useful as an agent for promoting adsorption of ingredient (A) to the gums or oral mucosa.

With respect to the above-described embodiments, the present invention further discloses the following oral compositions.

[1] An oral composition comprising the following ingredients (A), (B), (C), and (D):

(A) 0.01 mass % or more and 2.5 mass % or less of one or more oil-soluble medicinal ingredients selected from the group consisting of glycyrrhetinic acid, tocopherol, and a tocopherol derivative;

(B) 4 mass % or more and 30 mass % or less of a higher alcohol having 12 or more and 22 or less carbon atoms comprising (b1) cetanol and (b2) stearyl alcohol;

(C) 0.1 mass % or more and 10 mass % or less of a surfactant comprising one or more selected from the group consisting of (c1) a nonionic surfactant selected from the group consisting of sorbitan fatty acid ester and polyoxyethylene sorbitan fatty acid ester, and (c2) an anionic surfactant being a fatty acid having 12 or more and 22 or less carbon atoms or a salt thereof; and (D) water wherein a mass ratio of the content of (E) an oil agent other than ingredients (A), (B), and (C) and a flavoring agent to the content of ingredient (B), ((E)/(B)), is less than 1; and the content of (F) an abrasive powder comprising a polyvalent metal is 5 mass % or less.

[2] The oral composition according to aspect [1], wherein the content of ingredient (A) is preferably 0.02 mass % or more, more preferably 0.05 mass % or more, even more preferably 0.08 mass % or more and preferably 2.3 mass % or less, more preferably 1.5 mass % or less, even more preferably 1 mass % or less, further preferably 0.5 mass % or less, further more preferably 0.3 mass % or less.

[3] The oral composition according to aspect [1] or [2], wherein ingredient (A) preferably comprises glycyrrhetinic acid, and the content of the glycyrrhetinic acid is preferably 0.01 mass % or more, more preferably 0.02 mass % or more, even more preferably 0.05 mass % or more, further preferably 0.08 mass % or more and preferably 0.5 mass % or less, more preferably 0.3 mass % or less.

[4] The oral composition according to any one of aspects [1] to [3], wherein the content of ingredient (B) is preferably 4.5 mass % or more and preferably 25 mass % or less, more preferably 20 mass % or less, further preferably 18 mass % or less.

[5] The oral composition according to any one of aspects [1] to [4], wherein the mass ratio of the sum of the content of ingredient (b1) and the content of ingredient (b2) to the content of ingredient (B), (((b1)+(b2))/(B)), is preferably 0.85 or more, more preferably 0.9 or more, even more preferably 0.92 or more and preferably 1 or less.

[6] The oral composition according to any one of aspects [1] to [5], wherein the mass ratio of the content of ingredient (b1) to the content of ingredient (b2), ((b1)/(b2)), is preferably 0.5 or more, more preferably 0.7 or more and preferably 5 or less, more preferably 3 or less, even more preferably 2 or less, further preferably 1.7 or less.

[7] The oral composition according to any one of aspects [1] to [6], wherein ingredient (B) other than ingredient (b1) and ingredient (b2) is one or more selected from the group consisting of lauryl alcohol, myristyl alcohol, and behenyl alcohol; the mass ratio of the sum of the content of lauryl alcohol and the content of myristyl alcohol to the content of ingredient (B), ((lauryl alcohol+myristyl alcohol)/(B)), is preferably 0.05 or less, more preferably 0.03 or less, even more preferably 0.01 or less; and the mass ratio of the content of behenyl alcohol to the content of ingredient (B), (behenyl alcohol/(B)), is preferably 0.1 or less, more preferably 0.05 or less.

[8] The oral composition according to any one of aspects [1] to [7], wherein the mass ratio of the content of ingredient (A) to the content of ingredient (B), ((A)/(B)), is preferably 0.002 or more, more preferably 0.004 or more, more preferably 0.005 or more and preferably 0.5 or less, more preferably 0.4 or less, even more preferably 0.3 or less, further preferably 0.2 or less, further more preferably 0.15 or less.

[9] The oral composition according to any one of aspects [1] to [8], wherein the composition comprises glycyrrhetinic acid as ingredient (A); and the mass ratio of the content of the glycyrrhetinic acid to the content of ingredient (B), (glycyrrhetinic acid/(B)), is preferably 0.002 or more, more preferably 0.004 or more, more preferably 0.005 or more and preferably 0.1 or less, more preferably 0.075 or less, even more preferably 0.05 or less.

[10] The oral composition according to any one of aspects [1] to [9], wherein the content of ingredient (C) is preferably 0.2 mass % or more, more preferably 0.3 mass % or more, even more preferably 0.4 mass % or more, further more preferably 0.5 mass % or more and preferably 9 mass % or less, more preferably 8 mass % or less, even more preferably 7 mass % or less.

[11] The oral composition according to any one of aspects [1] to [10], wherein the composition comprises ingredient (c1) as ingredient (C); the mass ratio of the content of ingredient (B) to the content of a nonionic surfactant comprising ingredient (c1), ((B)/nonionic surfactant), is preferably 1 or more, more preferably 1.2 or more, even more preferably 1.4 or more and preferably 20 or less, more preferably 17 or less, even more preferably 15 or less; and the mass ratio when ingredient (c2) is not contained is preferably 10 or less, more preferably 5 or less, even more preferably 3.5 or less.

[12] The oral composition according to any one of aspects [1] to [11], wherein the composition comprises ingredient (c2) as ingredient (C); and the mass ratio of the content of ingredient (B) to the content of an anionic surfactant comprising ingredient (c2), ((B)/anionic surfactant), is preferably 3 or more, more preferably 4 or more, even more preferably 5 or more, further preferably 7 or more, further more preferably 10 or more and preferably 200 or less, more preferably 180 or less, even more preferably 90 or less, further preferably 18 or less.

[13] The oral composition according to any one of aspects [1] to [12], wherein the mass ratio of the content of ingredient (B) to the sum of the content of ingredient (c1) and the content of ingredient (c2) in terms of fatty acids, ((B)/((c1)+(c2))), is preferably higher than 1, more preferably 1.2 or more, even more preferably 1.5 or more and preferably 40 or less, more preferably 35 or less, even more preferably 30 or less.

[14] The oral composition according to any one of aspects [11] to [13], wherein the content of ingredient (c1) is preferably 0.2 mass % or more, more preferably 0.4 mass % or more, even more preferably 0.5 mass % or more and preferably 10 mass % or less, more preferably 8 mass % or less, even more preferably 6 mass % or less; when ingredient (c2) is not contained, the content of ingredient (c1) is preferably 1 mass % or more, more preferably 1.5 mass % or more, even more preferably 2 mass % or more; and when ingredient (c2) is contained, the content is preferably 5 mass % or less.

[15] The oral composition according to any one of aspects [1] to [14], wherein the content of ingredient (c2) is, in terms of fatty acids, preferably 0.05 mass % or more, more preferably 0.08 mass % or more, even more preferably 0.1 mass % or more, further preferably 0.2 mass % or more, further more preferably 1 mass % or more and preferably 5 mass % or less, more preferably 3 mass % or less, even more preferably 2.5 mass % or less, further preferably 2 mass % or less, further more preferably 0.5 mass % or less, further more preferably 0.2 mass % or less.

[16] The oral composition according to any one of aspects [1] to [15], wherein the sum of the content of ingredient (c1) and the content of ingredient (c2) in terms of fatty acids is preferably 0.1 mass % or more, more preferably 0.2 mass % or more, even more preferably 0.3 mass % or more, further preferably 0.4 mass % or more, further more preferably 0.5 mass % or more and preferably 10 mass % or less, more preferably 8 mass % or less, even more preferably 6.5 mass % or less.

[17] The oral composition according to any one of aspects [1] to [16], wherein the content of a cationic surfactant other than a cationic bactericide is preferably 0.1 mass % or less, more preferably 0.05 mass % or less, even more preferably 0.01 mass % or less; or the cationic surfactant other than the cationic bactericide is preferably not contained.

[18] The oral composition according to any one of aspects [1] to [17], wherein the content of the cationic bactericide is preferably 0.005 mass % or more, more preferably 0.01 mass % or more, even more preferably 0.02 mass % or more and preferably 0.1 mass % or less, more preferably 0.08 mass % or less, even more preferably 0.06 mass % or less.

[19] The oral composition according to any one of aspects [1] to [18], wherein the mass ratio of the content of the cationic bactericide to the content of ingredient (B), (cationic bactericide/ingredient (B)), is preferably 0.001 or more, more preferably 0.002 or more and preferably 0.02 or less, more preferably 0.01 or less.

[20] The oral composition according to any one of aspects [1] to [19], wherein the mass ratio of the content of the cationic bactericide to the content of the glycyrrhetinic acid, (cationic bactericide/glycyrrhetinic acid), is preferably 0.01 or more, more preferably 0.05 or more, even more preferably 0.1 or more and preferably 2 or less, more preferably 1.5 or less, even more preferably 1 or less, further preferably 0.8 or less.

[21] The oral composition according to any one of aspects [18] to [20], wherein the cationic bactericide is preferably a quaternary ammonium compound selected from the group consisting of cetyl pyridinium chloride, benzethonium chloride, benzalkonium chloride, stearyl dimethyl ammonium chloride, stearyl trimethyl ammonium chloride, cetyl trimethyl ammonium chloride, methyl benzethonium chloride, lauryl trimethyl ammonium chloride, and lauroyl colamino formyl methyl pyridinium chloride; more preferably one or more selected from the group consisting of cetyl pyridinium chloride, benzethonium chloride, and benzalkonium chloride; even more preferably cetyl pyridinium chloride.

[22] The oral composition according to any one of aspects [1] to [21], wherein the content of ingredient (D) is preferably 30 mass % or more, more preferably 40 mass % or more, even more preferably 50 mass % or more, further preferably 55 mass % or more and preferably 95 mass % or less, more preferably 92 mass % or less.

[23] The oral composition according to any one of aspects [1] to [22], wherein the mass ratio of the content of (E) the oil agent other than ingredients (A), (B), and (C) and the flavoring agent to the content of ingredient (B), ((E)/(B)), is preferably 0.5 or less, more preferably 0.3 or less.

[24] The oral composition according to any one of aspects [1] to [23], wherein the content of ingredient (E) is preferably 5 mass % or less, more preferably 2 mass % or less, even more preferably 1 mass % or less, further preferably 0.5 mass % or less; and when ingredient (E) is an oil that is a liquid at 25° C., the content of ingredient (E) is preferably 5 mass % or less, more preferably 3 mass % or less, even more preferably 2 mass % or less.

[25] The oral composition according to any one of aspects [1] to [24], wherein the content of (F) an abrasive comprising a polyvalent metal is preferably 3 mass % or less, more preferably 1 mass % or less; or ingredient (F) is not contained.

[26] The oral composition according to any one of aspects [1] to [25], wherein the content of a binder other than a cellulose binder is preferably 0.5 mass % or less, more preferably 0.3 mass % or less, even more preferably 0.2 mass % or less.

[27] The oral composition according to aspect [26], wherein the binder other than the cellulose binder is preferably one or more selected from the group consisting of sodium alginate, carrageenan, xanthan gum, sodium polyacrylate, pectin, agar, gum tragacanth, gum arabic, guar gum, karaya gum, locust bean gum, gella gum, tamarid gum, *psyllium* seed gum, and a carboxyvinyl polymer, more preferably one or two selected from the group consisting of carrageenan and xanthan gum.

[28] The oral composition according to any one of aspects [1] to [27], wherein the content of a carboxyvinyl polymer is preferably 0.3 mass % or less, more preferably 0.2 mass % or less, even more preferably 0.1 mass % or less, further preferably 0.05 mass % or less, further more preferably 0.01 mass % or less.

[29] The oral composition according to any one of aspects [1] to [28], wherein the content of a thickening silica is preferably 5 mass % or less, more preferably 3 mass % or less; and the content of fatty acid dextrin is preferably 3 mass % or less, more preferably 1.5 mass % or less.

[30] The oral composition according to any one of aspects [1] to [29], wherein the content of ethanol is preferably 8 mass % or less, more preferably 5 mass % or less, even more preferably 2 mass % or less; or ethanol is not contained.

[31] The oral composition according to any one of aspects [1] to [30], wherein the content of polyoxyethylene hydrogenated castor oil is preferably 0.5 mass % or less, more preferably 0.3 mass % or less, even more preferably 0.1 mass % or less, further preferably 0.01 mass % or less; or polyoxyethylene hydrogenated castor oil is not contained.

[32] The oral composition according to any one of aspects [1] to [31], wherein the content of a sugar alcohol is preferably 30 mass % or less, more preferably 20 mass % or less, even more preferably 15 mass % or less and preferably 1 mass % or more, more preferably 2 mass % or more, even more preferably 5 mass % or more.

[33] The oral composition according to any one of aspects [1] to [32], wherein the composition has a viscosity at 20° C. of preferably 5,000 dPa·s or less, more preferably 4,000 dPa·s or less, even more preferably 3,800 dPa·s or less and preferably 300 dPa·s or more, more preferably 400 dPa·s or more, even more preferably 500 dPa·s or more, further preferably 700 dPa·s or more.

[34] The oral composition according to any one of aspects [1] to [33], wherein the composition is a liquid dentifrice or toothpaste.

[35] A method of producing the oral composition according to any one of aspects [1] to [34], comprising a step of mixing a mixture liquid containing ingredient (B) and ingredient (C) at a temperature not lower than the melting point of ingredient (B) and not higher than 90° C., more preferably at a temperature not lower than the melting point of ingredient (B) and not higher than 85° C., further preferably at a temperature not lower than 80° C. and not higher than 85° C.

[36] The oral composition according to any one of aspects [1] to [34], wherein the composition is an agent for promoting adsorption of ingredient (A) to the gums or oral mucosa.

[37] Use of the oral composition according to any one of aspects [1] to [34] for promoting adsorption of ingredient (A) to the gums or oral mucosa.

[38] Use of the oral composition according to any one of aspects [1] to [34] for producing an agent for promoting adsorption of ingredient (A) to the gums or oral mucosa.

[39] A method for allowing adsorption of ingredient (A) to the gums or oral mucosa comprising applying the oral composition according to any one of aspects [1] to [34] to the oral cavity and preferably rinsing the oral cavity with water after the application.

EXAMPLES

The present invention will now be specifically described based on Examples. The content of each ingredient is represented by mass % unless otherwise specified in the Table.

Examples 1 to 20 and Comparative Examples 1 to 5

Each oral composition was produced according to the formulations shown in Tables 1 and 2. Specifically, ingredient (A), ingredient (B), and ingredient (C) were heated to 80° C. (80° C. to 82° C.) and were mixed, followed by stirring for about 10 minutes. Subsequently, ingredient (D) was added to and mixed with the mixture. Other ingredients were then added to and mixed for 10 minutes with the resulting mixture to give an oral composition.

Each of the resulting oral compositions was subjected to measurement of the viscosity and the amount of β-glycyrrhetinic acid adsorbed and the formation of α-gel was investigated, according to the following methods. The results are shown in Tables 1 and 2.

<<Measurement of Viscosity>>

Each of the resulting oral compositions was packed in a container for viscosity measurement and preserved in an incubator of 25° C. for 24 hours and was then subjected to measurement. The viscosity was measured at 25° C. with a Helipath viscometer (VISCOMETER TVB-10, Toki Sangyo Co., Ltd.) and a rotor T-C at a speed of 2.5 rpm for 1 minute.

<<Measurement of Amount of β-Glycyrrhetinic Acid Adsorbed>>

Each oral composition was preserved at room temperature (25° C.) for 24 hours since the preparation, and 2.0 g of the composition was then put into the inside of a glass cylinder with a diameter of 15 mm placed on a silicone sheet (20 mm×20 mm, thickness: 0.1 mm). After contacting for 30 seconds, 2 mL of purified water was added thereto, and the composition was sucked together with the purified water with a pipette. Similarly, washing with 2 mL of purified water was then performed twice. Subsequently, the silicone sheet was immersed in 1 mL of methanol and was shaken with a vortex mixer (SHIBATA TEST TUBE MIXER TTM-1, available from Shibata Scientific Technology Ltd.) for 30 seconds. The amount of f-glycyrrhetinic acid in methanol was measured by high-performance liquid chromatography (HPLC) under the following conditions.

A reference solution of a glycyrrhetinic acid was prepared by adding 0.1 g of β-glycyrrhetinic acid to a mobile phase (0.1 w/v % phosphoric acid-containing methanol (methanol:water=8:2)) to make a 100 mL and further diluting the resulting solution 200 times in volume with the mobile phase. The content of β-glycyrrhetinic acid was determined by the product of the ratio of the peak area (X) of the absorbance of β-glycyrrhetinic acid to the peak area (Y) of the reference solution measured by HPLC, (X/Y), and the β-glycyrrhetinic acid concentration (Z) of the reference solution: ((Z)×(X)/(Y)).

(Conditions for HPLC Measurement)

Apparatus: Hitachi High Performance Chromatogram Lachrom Elite

Column: LiChroCART 125-4.0 LiChrospher100 RP-18 (e) (5 μm) (Kanto Chemical Co., Inc.)

Column temperature: 40° C.

Mobile phase: 0.1 w/v % phosphoric acid-containing methanol (methanol:water=8:2)

Flow rate: 1.0 mL/min

Sample injection volume: 20 μL

Measurement wavelength: 250 nm

<<Confirmation of α-Gel Formation>>

Each of the resulting oral compositions was confirmed whether α-gel was formed or not by wide angle X-ray diffraction. Specifically, formation of α-gel was determined by one sharp diffraction peak appeared at a Bragg angle of about 21° to 22° in wide angle X-ray diffraction.

Figure 1:
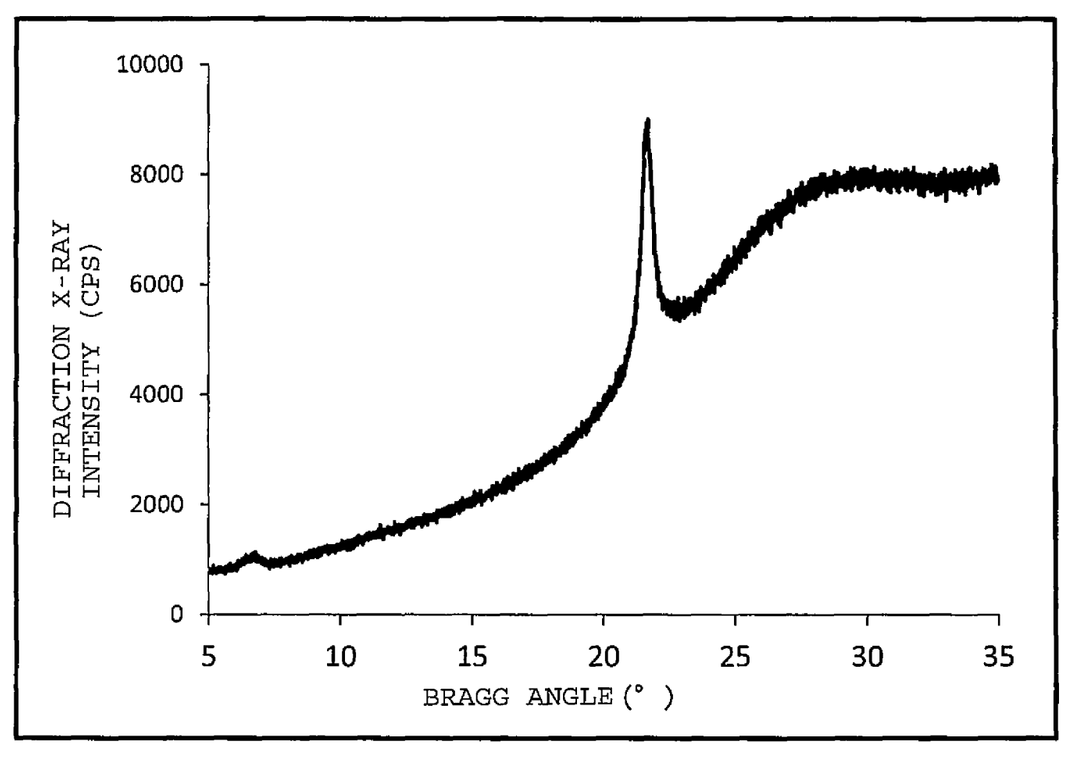
FIG. 1 is a graph showing a diffraction X-ray intensity distribution of the α-gel formed in the dentifrice obtained in Example 1 by wide angle X-ray diffraction.

Specifically, as also shown in FIG. 1, when one sharp diffraction peak was observed at a Bragg angle of about 21° to 23° indicating that the composition had an α-gel structure formed, the composition was evaluated as "Existed", and when such a peak was not observed, the composition was evaluated as "Not existed". FIG. 1 shows the diffraction X-ray intensity distribution in wide angle X-ray diffraction of the α-gel formed in the dentifrice of Example 1, but Comparative Examples 1, 2, 4, and 5 where separation was observed were not subjected to wide angle X-ray diffraction.

TABLE 1

| | | Example 1 | Example 2 | Example 3 | Example 4 | Example 5 | Example 6 | Example 7 | Example 8 | Example 9 | Example 10 | Example 11 | Example 12 | Example 13 | Example 14 | Example 15 |
|---|---|---|---|---|---|---|---|---|---|---|---|---|---|---|---|---|
| (A) | β-Glycyrrhetinic acid | 0.1 | 0.1 | 0.1 | 0.1 | 0.1 | 0.1 | 0.1 | 0.1 | 0.1 | 0.1 | 0.1 | 0.1 | 0.1 | 0.1 | 0.3 |
| | dl-α-Tocopherol acetate | | | | | | | | | | | | | | | 0.7 |
| (B) | Lauryl alcohol | 0.18 | 0.11 | 0.15 | 0.08 | 0.08 | 0.11 | 0.11 | 0.11 | 0.11 | 0.11 | 0.11 | 0.11 | 0.11 | 0.11 | 0.11 |
| | Myristyl alcohol | 0.32 | 0.24 | 0.33 | 0.16 | 0.16 | 0.24 | 0.24 | 0.24 | 0.24 | 0.24 | 0.24 | 0.24 | 0.24 | 0.24 | 0.24 |
| | Cetanol (b1) | 5.1 | 3.15 | 4.22 | 2.11 | 2.11 | 3.15 | 3.15 | 3.15 | 3.15 | 3.15 | 3.15 | 3.15 | 3.15 | 3.15 | 3.15 |
| | Stearyl alcohol (b2) | 6.4 | 4 | 5.3 | 2.65 | 1.65 | 4 | 4 | 4 | 4 | 4 | 4 | 4 | 4 | 4 | 4 |
| (C) | Polyoxyethylene (20) sorbitan monostearate*1 (c1) | 6 | 4 | 0.5 | 0.5 | 2.5 | | | | | | | 2.5 | 2.5 | 2.5 | 2.5 |
| | Polyoxyethylene (20) sorbitan monooleate*2 (c1) | | | | | | 2.5 | | | | | | | | | |
| | Sorbitan monooleate*3 (c1) | | | | | | | 4 | | | | | | | | |
| | Sorbitan sesquioleate*4 (c1) | | | | | | | | 5 | | | | | | | |
| | Sorbitan monostearate*5 (c1) | | | 1 | 1 | | | | | 5 | | | | | | |
| | Palmitic acid (c2) | | | | 0.5 | | | | | | 0.25 | | | | | |
| | Stearic acid (c2) | | | 0.1 | | | | | | | | 0.25 | | | | |
| | Potassium hydroxide (48%) | | | 0.04 | 0.18 | | | | | | 0.04 | 0.08 | | | | |

TABLE 1-continued

|  | Example 1 | Example 2 | Example 3 | Example 4 | Example 5 | Example 6 | Example 7 | Example 8 | Example 9 | Example 10 | Example 11 | Example 12 | Example 13 | Example 14 | Example 15 |
|---|---|---|---|---|---|---|---|---|---|---|---|---|---|---|---|
| (E) Liquid paraffin |  |  |  |  |  |  |  |  |  |  |  |  |  |  |  |
| Hydroxyethyl cellulose sodium |  |  |  |  |  |  |  |  |  |  |  | 0.1 |  |  |  |
| (F) Anhydrous calcium hydrogen phosphate |  |  |  |  |  |  |  |  |  |  |  |  | 3 | 2 | 1 |
| Sorbitol (70%) | 20 | 20 | 20 | 20 | 20 | 20 | 20 | 20 | 20 | 20 | 20 |  |  |  |  |
| Sodium saccharin | 0.04 | 0.04 | 0.04 | 0.04 | 0.04 | 0.04 | 0.04 | 0.04 | 0.04 | 0.04 | 0.04 |  |  |  |  |
| Flavoring agent | 1 | 1 | 1 | 1 | 1 | 1 | 1 | 1 | 1 | 1 | 1 | 1 | 1 | 1 | 1 |
| (D) Water | 60.86 | 67.36 | 67.22 | 71.68 | 72.36 | 68.86 | 67.36 | 66.36 | 66.36 | 71.07 | 71.03 | 88.8 | 85.9 | 86.9 | 88 |
| Total | 100 | 100 | 100 | 100 | 100 | 100 | 100 | 100 | 100 | 100 | 100 | 100 | 100 | 100 | 100 |
| (B) | 12 | 7.5 | 10 | 5 | 4 | 7.5 | 7.5 | 7.5 | 7.5 | 7.5 | 7.5 | 7.5 | 7.5 | 7.5 | 7.5 |
| (A)/(B) | 0.008 | 0.013 | 0.010 | 0.020 | 0.025 | 0.013 | 0.013 | 0.013 | 0.013 | 0.013 | 0.013 | 0.013 | 0.013 | 0.013 | 0.133 |
| (b1)/(b2) | 0.80 | 0.79 | 0.80 | 0.80 | 1.28 | 0.79 | 0.79 | 0.79 | 0.79 | 0.79 | 0.79 | 0.79 | 0.79 | 0.79 | 0.79 |
| (B)/((c1) + (c2)) | 2.0 | 1.9 | 6.3 | 2.5 | 1.6 | 3.0 | 1.9 | 1.5 | 1.5 | 30.0 | 30.0 | 3.0 | 3.0 | 3.0 | 3.0 |
| Helipath viscosity (dPa·s) | 3608 | 2640 | 3560 | 2136 | 1320 | 720 | 880 | 928 | 1064 | 1060 | 1096 | 2536 | 2496 | 1552 | 2656 |
| Amount of β-glycyrrhetinic acid adsorbed/ppm | 6.44 | 2.40 | 1.77 | 1.50 | 2.99 | 3.63 | 5.24 | 5.32 | 2.85 | 1.65 | 1.89 | 1.71 | 1.83 | 3.09 | 4.26 |
| α-Gel formation | Confirmed | Confirmed | Confirmed | Confirmed | Confirmed | Confirmed | Confirmed | Confirmed | Confirmed | Confirmed | Confirmed | Confirmed | Confirmed | Confirmed | Confirmed |

\*[1]Rheodol TW-S120V (20EO), manufactured by Kao Corporation
\*[2]Rheodol TW-O120V(20EO), manufactured by Kao Corporation
\*[3]Rheodol AO-10V, manufactured by Kao Corporation
\*[4]Rheodol AO-15V, manufactured by Kao Corporation
\*[5]Rheodol AS-10V, manufactured by Kao Corporation

TABLE 2

|   |   | Example 16 | Example 17 | Example 18 | Example 19 | Example 20 | Comparative Example 1 |
|---|---|---|---|---|---|---|---|
| (A) | β-Glycyrrhetinic acid | 0.1 | 0.1 | 0.1 | 0.1 | 0.1 | 0.1 |
|   | dl-α-Tocopherol acetate | 0.1 |   |   |   |   |   |
| (B) | Lauryl alcohol | 0.15 | 0.11 | 0.11 | 0.11 | 0.11 | 0.11 |
|   | Myristyl alcohol | 0.33 | 0.24 | 0.24 | 0.24 | 0.24 | 0.24 |
|   | Cetanol (b1) | 4.22 | 3.15 | 3.15 | 3.15 | 3.15 | 3.15 |
|   | Stearyl alcohol (b2) | 5.3 | 4 | 4 | 4 | 4 | 4 |
|   | Behenyl alcohol |   |   |   |   |   |   |
| (C) | Polyoxyethylene (20) sorbitan monostearate*1(c1) | 0.5 | 0.5 | 0.5 | 0.5 | 0.5 | 2.5 |
|   | Sorbitan sesquioleate*4(c1) | 1 |   |   |   |   |   |
|   | Sorbitan monostearate*5(c1) |   |   |   |   | 1 |   |
|   | Palmitic acid (c2) |   |   |   |   |   |   |
|   | Stearic acid (c2) | 0.5 |   | 0.1 | 0.1 | 0.1 |   |
|   | Polyoxyethylene (20) hydrogenated castor oil*6(c3) |   | 0.2 |   |   |   |   |
|   | Sodium lauryl sulfate (c4) |   |   | 0.5 |   |   |   |
|   | Ethanol |   |   |   |   | 1 |   |
|   | Potassium hydroxide (48%) |   | 0.04 | 0.04 | 0.04 | 0.04 |   |
|   | Sodium hydroxide (48%) | 0.2 |   |   |   |   |   |
| (E) | Liquid paraffin |   |   |   |   |   |   |
| (F) | Anhydrous calcium hydrogen phosphate |   |   |   |   |   | 10 |
|   | Sorbitol (70%) | 20 |   |   | 40 |   |   |
|   | Sodium saccharin | 0.04 |   |   |   |   |   |
|   | Flavoring agent | 1 | 1 | 1 | 1 | 1 | 1 |
| (D) | Water | 66.56 | 90.56 | 90.26 | 50.76 | 88.76 | 78.9 |
|   | Total | 100 | 100 | 100 | 100 | 100 | 100 |
|   | (B) | 10 | 7.5 | 7.5 | 7.5 | 7.5 | 7.5 |
|   | (A)/(B) | 0.020 | 0.013 | 0.013 | 0.013 | 0.013 | 0.013 |
|   | (b1)/(b2) | 0.80 | 0.79 | 0.79 | 0.79 | 0.79 | 0.79 |
|   | (B)/((c1) + (c2)) | 5.0 | 12.5 | 12.5 | 12.5 | 4.7 | 3.0 |
|   | Helipath viscosity (dPa·s) | 1224 | 1072 | 1040 | 1632 | 728 | 5632 |
|   | Amount of β-glycyrrhetinic acid adsorbed/ppm | 1.82 | 1.10 | 2.39 | 1.54 | 2.03 | 0.36 |
|   | α-Gel formation | Confirmed | Confirmed | Confirmed | Confirmed | Confirmed | Separated |

|   |   | Comparative Example 2 | Comparative Example 3 | Comparative Example 4 | Comparative Example 5 |
|---|---|---|---|---|---|
| (A) | β-Glycyrrhetinic acid | 0.1 | 0.1 | 0.1 | 0.1 |
|   | dl-α-Tocopherol acetate |   |   |   |   |
| (B) | Lauryl alcohol | 0.11 | 0.08 |   |   |
|   | Myristyl alcohol | 0.24 | 0.16 |   | 6 |
|   | Cetanol (b1) | 3.15 | 2.11 |   | 4 |
|   | Stearyl alcohol (b2) | 4 | 0.65 | 4.5 |   |
|   | Behenyl alcohol |   |   | 3 |   |
| (C) | Polyoxyethylene (20) sorbitan monostearate*1(c1) | 2.5 | 2.5 | 4 | 5 |
|   | Sorbitan sesquioleate*4(c1) |   |   | 1 | 1 |
|   | Sorbitan monostearate*5(c1) |   |   |   |   |
|   | Palmitic acid (c2) |   |   |   |   |
|   | Stearic acid (c2) |   |   | 0.5 | 0.5 |
|   | Polyoxyethylene (20) hydrogenated castor oil*6(c3) |   |   |   |   |
|   | Sodium lauryl sulfate (c4) |   |   |   |   |
|   | Ethanol |   |   |   |   |
|   | Potassium hydroxide (48%) |   |   | 0.04 | 0.04 |
|   | Sodium hydroxide (48%) |   |   |   |   |
| (E) | Liquid paraffin |   | 20 |   |   |
| (F) | Anhydrous calcium hydrogen phosphate |   |   |   |   |
|   | Sorbitol (70%) |   |   | 20 | 20 |
|   | Sodium saccharin |   |   | 0.04 | 0.04 |
|   | Flavoring agent | 1 | 1 | 1 | 1 |
| (D) | Water | 68.9 | 93.4 | 65.82 | 62.32 |
|   | Total | 100 | 100 | 100 | 100 |
|   | (B) | 7.5 | 3 | 7.5 | 10 |
|   | (A)/(B) | 0.013 | 0.033 | 0.013 | 0.010 |
|   | (b1)/(b2) | 0.79 | 3.25 | 0.00 | — |
|   | (B)/((c1) + (c2)) | 3.0 | 1.2 | 1.4 | 1.5 |

TABLE 2-continued

| | | | | |
|---|---|---|---|---|
| Helipath viscosity (dPa · s) | 88 | 96 | — | — |
| Amount of β-glycyrrhetinic acid adsorbed/ppm | 0.07 | 0.06 | —*7 | —*8 |
| α-Gel formation | Separated | Not comfirmed | Separated | Separated |

*1,*4,*5 the same as those in Table 1
*6 Emanon CH-40(40EO), manufactured by Kao Corporation
*7 Ingredient (B) was precipitated.
*8 Adsorption of β-glycyrrhetinic acid was not observed, and fatty acid smell was sensed.

Comparative Examples 6 and 7

Oral compositions were produced as in Example 1 according to the formulations shown in Table 3.

Each of the resulting oral compositions was subjected to measurement of the viscosity and the amount of β-glycyrrhetinic acid adsorbed according to the above-described methods.

The results, including those of Example 6, are shown in Table 3.

TABLE 3

| | | Example 6 | Comparative Example 6 | Comparative Example 7 |
|---|---|---|---|---|
| (A) | β-Glycyrrhetinic acid | 0.1 | 0.1 | 0.1 |
| (B) | Lauryl alcohol | 0.11 | 0.11 | 0.11 |
| | Myristyl alcohol | 0.24 | 0.24 | 0.24 |
| | Cetanol (b1) | 3.15 | 3.15 | 3.15 |
| | Stearyl alcohol (b2) | 4 | 4 | 4 |
| (C) | Polyoxyethylene (20) sorbitan monooleate*2(c1) | 2.5 | | |
| | Polyoxyethylene (20) hydrogenated castor oil*6(c3) | | 2.5 | |
| | Sodium lauryl sulfate (c4) | | | 2.5 |
| | Sorbitol (70%) | 20 | | |
| | Sodium saccharin | 0.04 | | |

TABLE 3-continued

| | Example 6 | Comparative Example 6 | Comparative Example 7 |
|---|---|---|---|
| Flavoring agent | 1 | 1 | 1 |
| (D) Water | 68.86 | 88.9 | 88.9 |
| Total | 100 | 100 | 100 |
| (B) | 7.5 | 7.5 | 7.5 |
| (A)/(B) | 0.013 | 0.013 | 0.013 |
| (b1)/(b2) | 0.79 | 0.79 | 0.79 |
| (B)/((c1) + (c2)) | 3.0 | — | — |
| Helipath viscosity (dPa · s) | 720 | 1680 | 752 |
| Amount of β-glycyrrhetinic acid adsorbed/ppm | 3.63 | 0.51 | 0.49 |

*2, *6 the same as those in Table 1

Examples 21 to 25 and Comparative Examples 8 and 9

Oral compositions were produced as in Example 1 according to the formulations shown in Table 4.

Each of the resulting oral compositions was subjected to measurement of the viscosity according to the above-described method, and the formation of α-gel was confirmed.

The results are shown in Table 4.

Comparative Examples 8 and 9 where separation was observed were not subjected to wide angle X-ray diffraction.

TABLE 4

| | | Example 21 | Example 22 | Example 23 | Example 24 | Comparative Example 8 | Comparative Example 9 | Example 25 |
|---|---|---|---|---|---|---|---|---|
| (A) | β-Glycyrrhetinic acid | 0.1 | 0.1 | 0.1 | 0.1 | 0.1 | 0.1 | 0.3 |
| | dl-α-Tocopherol acetate | | | | | | | |
| (B) | Cetanol (b1) | 6 | 10 | 6 | 6 | 10 | | 6 |
| | Stearyl alcohol (b2) | 4 | 7 | 4 | 4 | | | 4 |
| (C) | Polyoxyethylene (20) sorbitan monostearate*1(c1) | 0.5 | 0.5 | 0.5 | 0.5 | 0.5 | 0.5 | 0.5 |
| | Sorbitan monostearate*5(c1) | 1 | 2 | 1 | 1 | 1 | 1 | 2 |
| | Stearic acid (c2) | 0.1 | 0.1 | 0.1 | 0.1 | 0.1 | 0.1 | 0.1 |
| | Potassium hydroxide (48%) | 0.04 | 0.04 | 0.04 | 0.04 | 0.04 | 0.04 | 0.04 |
| | Vaseline | | | | | | 10 | |
| | Xanthan gum | 0.2 | 0.2 | 0.2 | 0.2 | 0.2 | 0.2 | 0.2 |
| | Thickening silica*9 | | | 2 | | | | |
| | Dextrin palmitate*10 | | | | 1 | | | |
| | Sorbitol | 20 | 20 | 20 | 20 | 20 | 20 | 20 |
| | Glycerin | 5 | 5 | 5 | 5 | 5 | 5 | 5 |
| | Sodium saccharin | 0.04 | 0.04 | 0.04 | 0.04 | 0.04 | 0.04 | 0.04 |
| | Flavoring agent | 1 | 1 | 1 | 1 | 1 | | 1 |
| (D) | Water | 62.02 | 54.02 | 60.02 | 61.02 | 62.02 | 63.02 | 60.82 |
| Total | | 100 | 100 | 100 | 100 | 100 | 100 | 100 |
| (B) | | 10 | 17 | 10 | 10 | 10 | 0 | 10 |
| (A)/(B) | | 0.010 | 0.006 | 0.010 | 0.010 | 0.010 | — | 0.030 |
| (b1)/(b2) | | 1.50 | 1.43 | 1.50 | 1.50 | — | — | 1.50 |
| (B)/((c1) + (c2)) | | 6.3 | 6.5 | 6.3 | 6.3 | 6.3 | 0.0 | 3.8 |

TABLE 4-continued

| | | Example 21 | Example 22 | Example 23 | Example 24 | Comparative Example 8 | Comparative Example 9 | Example 25 |
|---|---|---|---|---|---|---|---|---|
| Amount of β-glycyrrhetinic acid adsorbed/ppm | | 7.19 | 3.9 | 5.75 | 4.78 | —[11] | —[11] | 25.17 |
| α-Gel formation | | Confirmed | Confirmed | Confirmed | Confirmed | Separated | Separated | Confirmed |

[1],[5]the same as those in Table 1
[9]Sylopure 25, manufactured by Fuji Silysia Chemical Ltd.
[10]Rheopearl KL2, manufactured by Chiba Flour Milling Co., Ltd.
[11]Measurement was impossible due to precipitation of oil.

Example 26

An oral composition was produced as in Example 1 according to the formulation shown in Table 5.

The resulting oral composition was subjected to measurement of the viscosity and the amount of β-glycyrrhetinic acid adsorbed according to the above-described methods, and the formation of α-gel was confirmed.

The results, including those of Example 15 shown in Table 1, are shown in Table 5.

TABLE 5

| | | Example 15 | Example 26 |
|---|---|---|---|
| (A) | β-Glycyrrhetinic acid | 0.3 | 0.3 |
| | dl-α-Tocopherol acetate | 0.7 | 2.0 |
| (B) | Lauryl alcohol | 0.11 | |
| | Myristyl alcohol | 0.24 | |
| | Cetanol (b1) | 3.15 | 5.0 |
| | Stearyl alcohol (b2) | 4.0 | 3.0 |
| (C) | Polyoxyethylene (20) sorbitan monostearate*[1](c1) | 2.5 | 4.4 |
| | Sorbitol (70%) | | 10 |
| | Glycerin | | 20 |
| | Sodium saccharin | | 0.03 |
| | Cetyl pyridinium chloride | | 0.05 |
| | Flavoring agent | 1.0 | 0.5 |
| (D) | Water | 88.0 | 54.72 |
| Total | | 100 | 100 |
| (B) | | 7.5 | 8 |
| (A)/(B) | | 0.133 | 0.288 |
| (b1)/(b2) | | 0.79 | 1.67 |
| (B)/((c1) + (c2)) | | 3.0 | 1.8 |
| Helipath viscosity (dPa · s) | | 2656 | 3472 |
| Amount of β-glycyrrhetinic acid adsorbed/ppm | | 4.26 | 4.99 |
| α-Gel formation | | Confirmed | Confirmed |

*[1]the same as those in Table 1

Examples 27 to 29

Oral compositions were produced as in Example 1 according to the formulations shown in Table 6.

Each of the resulting oral compositions was subjected to measurement of the amount of β-glycyrrhetinic acid adsorbed according to the above-described method, and the formation of α-gel was confirmed.

The results are shown in Table 6.

TABLE 6

| | | Example 27 | Example 28 | Example 29 |
|---|---|---|---|---|
| (A) | β-Glycyrrhetinic acid | 0.1 | 0.1 | 0.1 |
| | dl-α-Tocopherol acetate | 0.1 | 0.1 | 0.1 |
| (B) | Lauryl alcohol | | | |
| | Myristyl alcohol | | | |

TABLE 6-continued

| | | Example 27 | Example 28 | Example 29 |
|---|---|---|---|---|
| | Cetanol (b1) | 9 | 9 | 9 |
| | Stearyl alcohol (b2) | 6 | 6 | 6 |
| (C) | Polyoxyethylene (20) sorbitan monostearate*[1](c1) | 0.5 | 0.5 | 0.5 |
| | Sorbitan monostearate*[5](c1) | 3 | 3 | 3 |
| | Palmitic acid (c2) | | | 2 |
| | Stearic acid (c2) | | 2 | |
| | Myristic acid (c2) | 2 | | |
| | Sodium hydroxide (48%) | 1 | 1 | 1 |
| | Sorbitol (70%) | 20 | 20 | 20 |
| | Glycerin | 5 | 5 | 5 |
| | Sodium saccharin | 0.03 | 0.03 | 0.03 |
| | Cetyl pyridinium chloride | 0.05 | 0.05 | 0.05 |
| | Flavoring agent | 1.2 | 1.2 | 1.2 |
| (D) | Water | 52.12 | 52.12 | 52.12 |
| Total | | 100 | 100 | 100 |
| (B) | | 15.5 | 15.5 | 15.5 |
| (A)/(B) | | 0.013 | 0.013 | 0.013 |
| (b1)/(b2) | | 1.50 | 1.50 | 1.50 |
| (B)/((c1) + (c2)) | | 2.8 | 2.8 | 2.8 |
| Amount of β-Glycyrrhetinic acid adsorbed/ppm | | 4.73 | 7.37 | 7.975 |
| α-Gel formation | | Existed | Existed | Existed |

*[1], *[5]the same as those in Table 1

Examples 30 and 31

Oral compositions were produced as in Example 1 according to the formulations shown in Table 7. Each of the resulting oral compositions was subjected to measurement of the viscosity and the amount of β-glycyrrhetinic acid adsorbed according to the above-described methods, and the formation of α-gel was confirmed.

The results are shown in Table 7.

TABLE 7

| | | Example 30 | Example 31 |
|---|---|---|---|
| (A) | β-Glycyrrhetinic acid | 0.1 | 0.1 |
| | dl-α-Tocopherol acetate | | |
| (B) | Lauryl alcohol | 0.15 | 0.15 |
| | Myristyl alcohol | 0.33 | 0.33 |
| | Cetanol (b1) | 4.22 | 4.22 |
| | Stearyl alcohol (b2) | 5.3 | 5.3 |
| (C) | Polyoxyethylene (20) sorbitan monostearate*[1] (c1) | 0.5 | 0.5 |
| | Sorbitan monostearate*[5](c1) | 1.0 | 1.0 |
| | Stearic acid (c2) | 0.1 | 0.1 |
| | Sodium hydroxide (48%) | 0.04 | 0.04 |
| | Sorbitol (70%) | 20 | 20 |
| | Sodium saccharin | 0.04 | 0.04 |
| | Cetyl pyridinium chloride | 0 | 0.05 |
| | Flavoring agent | 1.0 | 1.0 |

TABLE 7-continued

|  |  | Example 30 | Example 31 |
|---|---|---|---|
| (D) | Water | 67.32 | 67.27 |
| Total |  | 100 | 100 |
| (B) |  | 10.35 | 10.35 |
| (A)/(B) |  | 0.010 | 0.010 |
| (b1)/(b2) |  | 0.80 | 0.80 |
| (B)/((c1) + (c2)) |  | 6.5 | 6.5 |
| Helipath viscosity (dPa · s) |  | 3,560 | 3,560 |
| Amount of β-glycyrrhetinic acid adsorbed/ppm |  | 1.77 | 2.14 |
| α-Gel formation |  | Confirmed | Confirmed |

*1, *5 the same as those in Table 1

Example 32

An oral composition of the following formulation was produced, and the formation of α-gel was confirmed.

TABLE 8

| Ingredient | (mass %) |
|---|---|
| β-Glycyrrhetinic acid | 0.1 |
| dl-α-Tocopherol acetate | 0.2 |
| Cetanol | 7.5 |
| Stearyl alcohol | 5 |
| Polyoxyethylene (20) sorbitan monostearate *1 | 0.5 |
| Sorbitan monostearate *5 | 3 |
| Stearic acid | 2 |
| Glycerin | 15 |
| Sodium hydroxide (48%) | 0.85 |
| Sorbitol (70%) | 10 |
| Sodium saccharin | 0.04 |
| Flavoring agent | 1 |
| Water | 54.81 |
| Total | 100 |

*1, *5: the same as those in Table 1

These results demonstrate that the dentifrice of each Example effectively forms α-gel and effectively increases the adsorption performance of ingredient (A) to the gums or oral mucosa.

The invention claimed is:

1. A method for improving periodontitis and periodontal disease, comprising applying an oral composition to gums or oral mucosa, wherein the oral composition comprises the following ingredients (A), (B), (C), and (D):
(A) 0.01 mass % to 2.5 mass % of one or more oil-soluble medicinal ingredients selected from the group consisting of glycyrrhetinic acid, tocopherol, and a tocopherol derivative;
(B) 4 mass % to 30 mass % of a higher alcohol having 12 to 22 carbon atoms comprising (b1) cetanol and (b2) stearyl alcohol;
(C) 0.1 mass % to 10 mass % of a surfactant comprising one or more selected from the group consisting of (c1) a nonionic surfactant selected from the group consisting of sorbitan fatty acid ester and polyoxyethylene sorbitan fatty acid ester, and (c2) an anionic surfactant being a fatty acid having 12 to 22 carbon atoms or a salt thereof; and
(D) water,
wherein a mass ratio of the content of (E) an oil agent other than ingredients (A), (B), and (C) and a flavoring agent to the content of ingredient (B), ((E)/(B)), is less than 1; and
the content of an abrasive powder (F) comprising a polyvalent metal is 5 mass % or less.

2. The method according to claim 1, wherein a mass ratio of the content of ingredient (B) to the sum of the content of ingredient (c1) and the content of ingredient (c2) in terms of fatty acids, ((B)/((c1)+(c2))), is more than 1 and 40 or less.

3. The method according to claim 1, wherein a mass ratio of the content of ingredient (b1) to the content of ingredient (b2), ((b1)/(b2)), is in a range of 0.5 to 5.

4. The method according to claim 1, wherein a mass ratio of the sum of the content of ingredient (b1) and the content of ingredient (b2) to the content of ingredient (B), (((b1)+(b2))/(B)), is in a range of 0.85 to 1.

5. The method according to claim 1, wherein the content of a cellulose binder is 0.3 mass % or less.

6. The method according to claim 1, wherein the cellulose binder is one or two selected from the group consisting of hydroxyalkyl cellulose and sodium carboxymethyl cellulose.

7. The method according to claim 1, wherein the content of an abrasive silica is 7 mass % or less.

8. The method according to claim 1, wherein the content of ingredient (D) is in a range of 50 mass % to 95 mass %.

9. The method according to claim 1, wherein the composition has a viscosity at 20° C. of 300 dPa·s to 5,000 dPa·s.

10. The method according to claim 1, wherein the content of polyoxyethylene hydrogenated castor oil is 0.5 mass % or less.

11. The method according to claim 1, wherein a mass ratio of the content of ingredient (A) to the content of ingredient (B), ((A)/(B)), is in a range of 0.002 to 0.2.

12. The method according to claim 1, wherein the content of a thickening silica is 5 mass % or less.

13. The method according to claim 1, wherein the content of one or more sugar alcohols selected from the group consisting of sorbitol, xylitol, erythritol, reduced palatinose, and mannitol is 30 mass % or less.

14. The method according to claim 1, wherein the composition comprises glycyrrhetinic acid as ingredient (A) and the content of the glycyrrhetinic acid is in a range of 0.08 mass % to 0.5 mass %.

15. The method according to claim 14, wherein a mass ratio of the content of glycyrrhetinic acid to the content of ingredient (B), (glycyrrhetinic acid/(B)), is in a range of 0.005 to 0.05.

16. The method according to claim 1, wherein the composition comprises ingredient (c1) as ingredient (C) and a mass ratio of the content of ingredient (B) to the content of a nonionic surfactant comprising ingredient (c1), ((B)/nonionic surfactant), is in a range of 1 to 20.

17. The method according to claim 1, wherein the composition comprises ingredient (c2) as ingredient (C) and a mass ratio of the content of ingredient (B) to the content of an anionic surfactant comprising ingredient (c2), ((B)/anionic surfactant), is in a range of 3 to 200.

18. The method according to claim 1, wherein a mass ratio of the content of ingredient (B) to the sum of the content of ingredient (c1) and the content of ingredient (c2), ((B)/((c1)+(c2))), is higher than 1 and 40 or less.

* * * * *